United States Patent [19]

Olsen

[11] Patent Number: 5,573,795
[45] Date of Patent: Nov. 12, 1996

[54] METHOD FOR TREATMENT OF POTATO FRUIT WATER

[75] Inventor: Hans S. Olsen, Holte, Denmark

[73] Assignee: Novo Nordisk A/S, Bagsvaerd, Denmark

[21] Appl. No.: 256,323

[22] PCT Filed: Jan. 28, 1993

[86] PCT No.: PCT/DK93/00030

§ 371 Date: Jul. 8, 1994

§ 102(e) Date: Jul. 8, 1994

[87] PCT Pub. No.: WO93/15616

PCT Pub. Date: Aug. 19, 1993

[30] Foreign Application Priority Data

Feb. 6, 1992 [DK] Denmark .................................. 0141/92

[51] Int. Cl.⁶ ............................. A23B 7/10; A23K 1/14; A23L 1/09; A23J 1/16
[52] U.S. Cl. .................. 426/53; 426/54; 426/63; 426/51; 426/52; 435/274; 435/275; 435/267; 435/277
[58] Field of Search ................... 426/53, 52, 51, 426/54; 435/274, 275, 267, 277

[56] References Cited

U.S. PATENT DOCUMENTS

| | | | |
|---|---|---|---|
| 4,421,682 | 12/1983 | Edwards et al. | 260/112 R |
| 4,478,940 | 10/1984 | Adler-Nissen et al. | 426/52 |
| 4,483,874 | 11/1984 | Olsen | 426/44 |

OTHER PUBLICATIONS

G. Richter et al., "Enzymatische Prozesse bei der Verarbeitung von Kartoffeln", vol. 35, No. 4, pp. 113–118, 1983.

*Primary Examiner*—Esther M. Kepplinger
*Assistant Examiner*—Choon P. Koh
*Attorney, Agent, or Firm*—Steve T. Zelson, Esq.; James J. Harrington, Esq.

[57] ABSTRACT

In the method for treatment of potato fruit water the potato fruit water is subjected to a heat treatment to at least 125° C. for at least 3 minutes, whereafter the heat treated potato fruit water is cooled to a temperature, at which enzymes are relatively stable, then enzymatically treated with a proteinase, and finally concentrated to microbial stability. Hereby a method for treatment of potato fruit water, which will enable a commercially sound utilization of potato fruit water, is provided.

13 Claims, 2 Drawing Sheets

5,573,795

METHOD FOR TREATMENT OF POTATO FRUIT WATER

BACKGROUND OF THE INVENTION

The invention comprises a method for treatment of potato fruit water (potato waste water). Potato fruit water is a certain fraction which appears during the potato starch production. The disintegrated, clean potato chips are first introduced into a decanter, the supernatant therefrom being the potato fruit water; the residue is introduced into a centrifugal sieve, from which two fractions are taken out, i.e. the potato starch fraction and the potato pulp fraction. The annual production of potato starch on a global basis is at least around $10^6$ tons, and the corresponding volume of potato fruit water is at least around $4 \times 10^6$ tons, with a dry matter content of at least $10^5$ tons.

Before the strict environmental regulations enforced today were passed, potato fruit water was simply fed into the sewer system or sprayed onto the fields. Another prior art attempt to solve the problem comprising the utilization of potato fruit water in an environmentally acceptable and economically sound manner has been established by utilization of heat coagulators with subsequent recovery of the insoluble part of the protein fraction by centrifugation as a concentrated protein precipitate. Also attempts have been made to use ultrafiltration of the potato fruit water in some potato processing plants. As around 50% of the total amount of the potato protein is low molecular and non-coagulable, the mentioned methods leave the non precipitable protein and the low molecular protein components in solution. Thus these unwanted products will be present in the waste water which has to be treated in waste water treatment plants or utilized by other means. After introduction of the enviromental regulations in many countries it became necessary to purify the potato fruit water as efficient as possible before it was introduced into the sewer system. This was a costly procedure, and the potato starch manufacturer could derive no benefit from this expense unless valuable products could be generated. It was suggested to concentrate the potato fruit water in order to use it as an animal fodder; however, as the potato fruit water without protein separation could not be concentrated more than corresponding to about 25% dry matter, due to a sharp viscosity rise, and as this percentage was considered too low for practical utilization of the concentrated potato fruit water as an animal fodder, this suggestion did never lead to a commercially sound utilization of potato fruit water.

SUMMARY OF THE INVENTION

Thus the purpose of the invention is the provision of a method for treatment of potato fruit water, which will enable a commercially sound utilization of potato fruit water.

The method according to the invention for treatment of potato fruit water is characterized by the fact that the potato fruit water is subjected to a heat treatment to at least 125° C. for at least 3 minutes, whereafter the heat treated fruit water is cooled to a temperature, at which enzymes are relatively stable, then enzymatically treated with a proteinase, and finally concentrated to microbial stability. The concentrated end product is either a concentrated liquid with a content of dry matter of 70% w/w or above, or a particle shaped material, such as a powder or a granulate.

No upper limit for the duration of the heat treatment is given; however, it is a known fact that a heat treatment with a duration above a certain critical value for this system, dependent of i.a. the pH, of the order of magnitude around 10 minutes, will give rise to an unwanted reaction between proteins and sugars (Maillard compositions), which will reduce the nutritional value of the end product which is concentrated to microbial stability.

Surprisingly it has been found that the potato fruit water, which is treated according to the invention, can be concentrated to a dry matter content of at least 50%, before the viscosity of the concentrate increases so much that fouling and solidification occurs and that the thus treated potato fruit water can be used in a commercially sound manner as a microbially stable fodder. Also, surprisingly it has been found that both the heat treatment and the enzyme treatment have to be carried out in order to obtain the desired result.

Documentation for the fact that the method according to the invention enables a sounder commercial utilization of the potato fruit water than the most common prior art method for treatment of potato fruit water is presented later in this specification.

DETAILED DESCRIPTION OF THE DRAWINGS

DESCRIPTION OF THE PREFERRED EMBODIMENT

Figure 1:
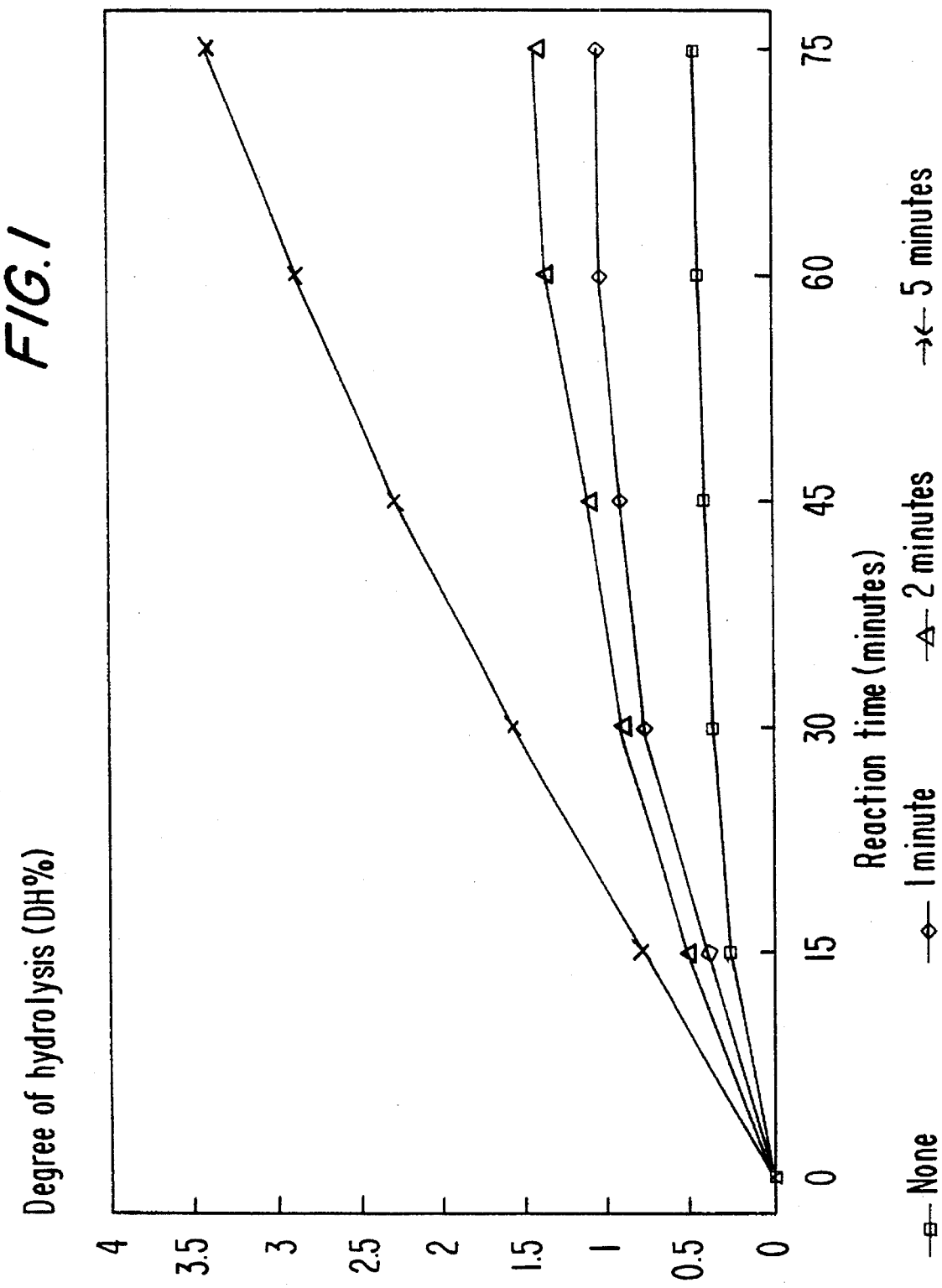
FIG. 1 shows the dependency between the degree of hydrolysis of the potato fruit water proteins by the proteolytic treatment and the hydrolysis reaction time, at different heat treatment times, with specific reference to Example 1.

In a preferred embodiment of the method according to the invention the potato fruit water is preconcentrated, either directly upstream the heat treatment or directly downstream the heat treatment. Directly upstream the heat treatment means between the heat treatment and the decantation, and directly downstream the heat treatment means between the heat treatment and the enzymatic reaction. The preconcentration can be carried out by evaporation or osmosis. In this manner a smaller liquid volume during the enzymatic hydrolysis is obtained, which is an advantage from an investment point of view. Also, in this manner, a smaller enzyme dosage can be used, and thus a more economic process can be obtained.

In a preferred embodiment of the method according to the invention the heating is carried out in a jet cooker. This is a convenient and effective manner for performing the heating. A jet cooking process is a special heat treatment in which efficient shearing and heating with direct steam is achieved with continuous flow through a combining tube. A typical commercial jet cooker, which can be used in the method according to the invention is Hydroheater®.

In a preferred embodiment of the method according to the invention the potato fruit water is heated to at least 130° C. for at least 3 minutes, preferably for at least 5 minutes. In this manner viscosity problems are reduced in a very efficient manner.

In a preferred embodiment of the method according to the invention the heat treated fruit water is cooled to a temperature between 60° C. and 45° C. In this manner it is secured that the enzymatic treatment is performed satisfactorily.

In a preferred embodiment of the method according to the invention the enzymatic treatment of the potato fruit water also comprises treatment with a starch degrading enzyme.

Hereby an even lower viscosity after the enzyme reaction can be obtained.

In a preferred embodiment of the method according to the invention the enzymatic treatment of the potato fruit water also comprises treatment with a cell wall degrading enzyme. Hereby an even lower viscosity after the enzyme reaction can be obtained.

In a preferred embodiment of the method according to the invention the protease is a neutral or alkaline protease and the enzymatic treatment is carried out at a constant pH at or close to the activity optimum of the enzyme. Examples of neutral or alkaline enzymes are Neutrase®, Alcalase®, Savinase® and Esperase®. Hereby an efficient degradation of the potato proteins is obtained.

In a preferred embodiment of the method according to the invention the cell wall degrading enzyme is an SPS-ase preparation and the protease is Alcalase® protease. This selection of cell wall degrading enzyme and proteinase has been found to be efficient in regard to enzymatic degradation.

In a preferred embodiment of the method according to the invention the enzymatic treatment is carried out sequentially and with pH adjustment in order to obtain optimal activities of the enzymes. In this manner the utilization of the enzymatic activities is optimal.

In a preferred embodiment of the method according to the invention the enzymatic reaction time is between 1 and 6 hours, preferably between 2 and 3 hours. If the reaction time is above 6 hours, the risk for putrefaction increases, and if the reaction time is less than 1 hour, the cost of the necessary amount of enzymes is will be unreasonably high.

In a preferred embodiment of the method according to the invention the enzyme or enzymes are not totally inactivated at the end of the enzymatic treatment. In this manner the enzymatic degradation can continue during the concentration of the treated potato fruit water, and due to the increasingly high concentration of dry matter during the concentration the enzyme stability and thus the wanted degradation is high.

In a preferred embodiment of the method according to the invention the concentrated material is spraydried. This is most convenient for transportation and use as a fodder.

The parts of Example 1, which describe the method without any enzyme addition or without jet cooking, are to be considered as comparisons outside the scope of the invention.

In Examples 1 and 2 which exclusively demonstrate the effect of .the enzyme(s) no final concentration to microbial stability was carried out; in Examples 3 and 4 the final concentration to microbial stability was carried out. Example 4 was exclusively carried out in pilot plant. Example 5 was carried out in order to illustrate the effect of various alkaline proteases.

EXAMPLE 1

5000 liters of potato fruit water (1.30% dry matter, 0.76% N×6.25) was centrifuged on a solids ejecting centrifuge type Westfalia SC 35 to remove residual starch. The centrifugate was evaporated to approximately 400 liter (10% dry matter was aimed at) on a falling film evaporator (Niro Atomizer type FF 200).

The thus produced concentrate was jet cooked by means of a Hydroheater® at T=130° C. and with a holding section which could be adjusted for a treatment time of 1 minute, 2 minutes and 5 minutes. The cooked product was continuously cooled through a plate heat exchanger to 50° C. Samples of this pre-evaporated and jet cooked potato fruit water concentrate (PJPFWC) and a sample of non-jet cooked potato fruit water concentrate were used for the following laboratory tests with the protease Alcalase® or with the cell wall degrading enzyme SP-311 + Alcalase®. Reference is made to H. Sejr Olsen: Aqueous extraction of oil from seeds. In report EUR 11583 EN, Agriculture. Agricultural refineries—A bridge from farm to industry, Edited by L. Munch and F. Rexen, sponsored by the Commision of the European Communities. (1990) (SP-311) and Product sheet from Novo Enzyme Process division B 318b-GB (Alcalase®). SP-311 is a liquid preparation with an SPS-ase activity of 50.00 SPSU/g of liquid preparation.

Laboratory Tests 800 g of PJPFWC was transferred to a 1 liter stirred reaction vessel, termostatted to 50° C. and adjusted to pH=4.50 by means of 6N HCl for treatment with SP-311 and to pH=8.0 by means of 4N NaOH for treatment with Alcalase®. During the treatment with Alcalase® pH was kept constant at pH=8.0 by means of a pH-stat. The amount of 4N NaOH used was recorded. Treatment with SP-311 was carried out for 24 hours and treatment with Alcalase® was carried out for up to 150 minutes. Based on the recorded amounts of 4N NaOH used for hydrolysis of the protein a hydrolysis curve was drawn up for the DH% (DH = degree of hydrolysis) versus time. The DH value was calculated by means of the following formula:

$$DH = \frac{1}{a \times h_{tot}} \times \frac{B \times N_B}{MP} \times 100\%$$

where

B=consumption of base in mls $N_B$=normality of base

MP=mass of protein (N×6.25) in grams

α=degree of dissociation $h_{tot}$=the total number of peptide bonds per weight unit of the protein (the value 8 g equivalents per kg of protein is used here).

Treatment with Alcalase® alone (no treatment with SP-311)

The effect of the jet cooking time on the performance of the hydrolysis of the potato protein appear from the following data:

Effect of jet-cooking and proteinase treatment of potato fruit water

Enzyme: Alcalase® 2.4 L, Dosage, % E/P=2.00 (E is the weight of the enzyme preparation, P is the weight of the substrate, in case the protein (N×6.25)) pH-stat, pH=8.00, 4N NaOH. Temperature T=50° C.

Jet cooking temperature 130° C.

| Jet cooking holding time (minutes) | 0 | 1 | 2 | 5 |
|---|---|---|---|---|
| % N×6.25 | 6.35 | 4.32 | 4.31 | 4.24 |
| Reaction Time (minutes) | ml NaOH | ml NaOH | ml NaOH | ml NaOH |
| 0 | 0.00 | 0.00 | 0.00 | 0.00 |
| 15 | 0.30 | 0.30 | 0.40 | 0.60 |
| 30 | 0.40 | 0.60 | 0.70 | 1.20 |
| 45 | 0.45 | 0.70 | 0.85 | 1.75 |
| 60 | 0.50 | 0.80 | 1.05 | 2.20 |
| 75 | 0.53 | 0.80 | 1.10 | 2.60 |
| Reaction Time (minutes) | DH % | DH % | DH % | DH % |
| 0 | 0.00 | 0.00 | 0.00 | 0.00 |
| 15 | 0.26 | 0.38 | 0.51 | 0.78 |
| 30 | 0.35 | 0.77 | 0.90 | 1.57 |

| Jet cooking holding time (minutes) | 0 | 1 | 2 | 5 |
|---|---|---|---|---|
| % Nx6.25 | 6.35 | 4.32 | 4.31 | 4.24 |
| 45 | 0.39 | 0.90 | 1.09 | 2.28 |
| 60 | 0.44 | 1.02 | 1.35 | 2.87 |
| 75 | 0.46 | 1.02 | 1.41 | 3.39 |

These data are further illustrated on FIG. 1, from which is appears that the treatment for 5 minutes exhibits the greatest effect on the hydrolysis of the protein part of the potato fruit water.

Treatment with Alcalase® and SP-311

Effect of jet cooking of pilot plant evaporated potato fruit water.

Enzyme 1: SP-311, Dosage, % E/D: 1.60 (D is the weight of the dry matter)
Enzyme 2: Alcalase® 2.4 L, Dosage, % E/P: 2.00
Reaction parameters:
Enzyme 1: pH=4.5, T=50° C., reaction time: 24 hours
Enzyme 2: pH-stat, pH=8.00, 4N NaOH, T=50° C.
Jet cooking temperature 130° C. with a holding time of 5 minutes.

| Enzyme Nx6.25 | None 6.35 | Enzyme 1 + 2 4.23 | Enzyme 2 4.23 |
|---|---|---|---|
| Reaction Time (minutes) | ml NaOH | ml NaOH | ml NaOH |
| 0 | 0.00 | 0.00 | 0.00 |
| 15 | 0.30 | 0.70 | 0.45 |
| 30 | 0.38 | 1.25 | 0.70 |
| 45 | 0.45 | 1.65 | 0.95 |
| 60 | 0.50 | 2.00 | 1.15 |
| 75 | 0.53 | 2.28 | 1.35 |
| 90 | | 2.50 | 1.55 |
| 105 | | 2.70 | 1.80 |
| 120 | | 2.90 | 2.00 |
| 135 | | 3.00 | 2.15 |
| 150 | | 3.10 | |
| Reaction Time (minutes) | DH % | DH % | DH % |
| 0 | 0.00 | 0.00 | 0.00 |
| 15 | 0.26 | 0.92 | 0.59 |
| 30 | 0.33 | 1.63 | 0.92 |
| 45 | 0.39 | 2.16 | 1.24 |
| 60 | 0.44 | 2.62 | 1.50 |
| 75 | 0.46 | 2.98 | 1.77 |
| 90 | | 3.27 | 2.03 |
| 105 | | 3.53 | 2.35 |
| 120 | | 3.79 | 2.62 |
| 135 | | 3.92 | 2.81 |
| 150 | | 4.05 | |

Figure 2:
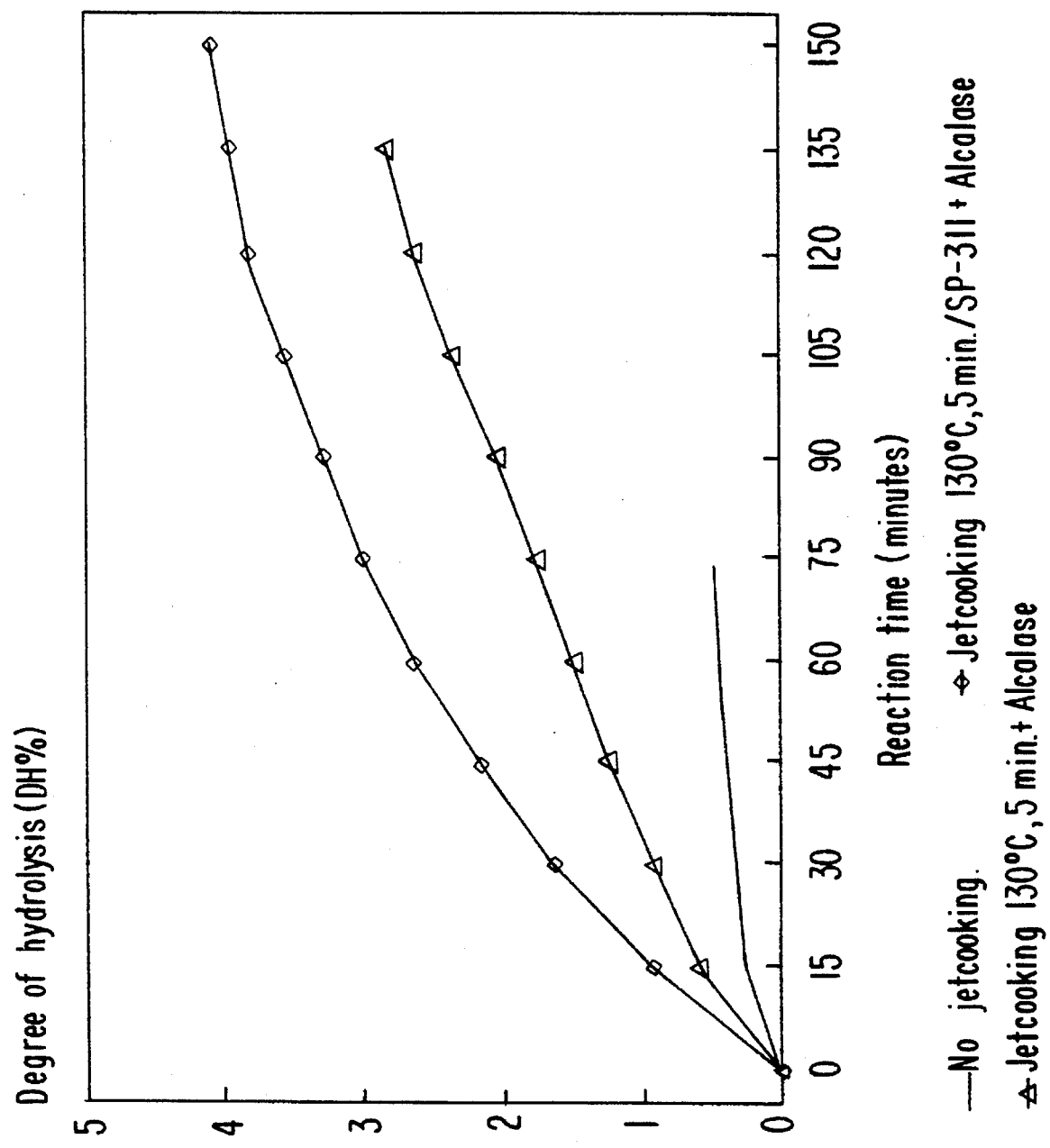
FIG. 2 shows the dependency between the degree of hydrolysis of the potato fruit water proteins by the enzymatic treatment and the hydrolysis reaction time 1) with no jet cooking and no enzyme (control), 2. with jet cooking and proteolytic enzyme, and 3) with jet cooking and both protcolytic enzyme and cell wall degrading enzyme, with specific reference to Example 1.

These data are further illustrated on FIG. 2, from which it appears that jet cooking and the treatment with SP-311 and Alcalase ® exhibits the greatest effect on the hydrolysis of the protein part of the potato fruit water.

EXAMPLE 2

5000 liters of potato fruit water (1.30% dry matter, 0.76% Nx6.25) was centrifuged on a solids ejecting centrifuge type Westfalia SC 35 to remove residual starch. The centrifugate was evaporated to approximately 400 liters (10% dry matter was aimed at) on a falling film evaporator (Niro Atomizer type FF 150).

The concentrate was jet cooked at T=130° C. for 5 minutes by means of a Hydroheater® and a holding section and subsequently continuously cooled to 50° C. through a plate heat exchanger. Samples of this pre-evaporated and jet cooked potato fruit water concentrate (PJPFWC) were used for the following laboratory tests in order to select an effective enzyme system.

Laboratory tests:

800 g of PJPFWC was transferred to a 1 liter stirred reaction vessel, termostatted to 50° C. and adjusted to pH=4.50 by means of 6N HCl for treatment with SP-311 or SP-348 (a *Humicola insolens* cellulase experimental preparation, vide Bio-Feed Plus B 402c-GB) and to pH=8.0 by means of 4N NaOH for treatment with Alcalase®. During the treatment with Alcalase® pH was kept constant at pH=8.0 by means of a pH-stat. Treatment with SP-311 or SP-348 was carried out for 24 hours and treatment with Alcalase® was carried out for 2 hours. After the enzyme treatments a portion of the reaction mixture was centrifuged at 3000×G (G=acceleration of earth gravity) for 30 minutes. The mass of the centrifugate was measured. Analyses were taken of the reaction mixture before centrifugation and of the centrifugate for analyses of total dry matter (DM) and nitrogen (Kjeldahl-N). Protein was calculated as Nx6.25.

The effect of the enzyme treatments is demonstrated in the tables below:

Data from the reaction mixture:

| Enzymes | | | Reaction mixture | |
|---|---|---|---|---|
| % of DM | % of protein | mass (g) | % dry matter | % protein |
| SP-311 | Alcalase ® 2.4 L | | | |
| 0 | 0 | 110.4 | 10.02 | 4.51 |
| 1.6 | 0 | 111.6 | 9.48 | 4.35 |
| 1.6 | 0 | 109.2 | 9.35 | 4.22 |
| 0 | 2 | 111.0 | 10.02 | 4.51 |
| 1.6 | 2 | 117.2 | 9.35 | 4.22 |
| | | | P/DM av. | 0.45 |
| SP-348 | Alcalase ® 2.4 L | | | |
| 1.6 | 0 | 143.5 | 9.76 | 4.42 |
| 1.6 | 2 | 144.1 | 9.76 | 4.42 |

Data from the supernatants:

| Enzymes | | Supernatants | | | | Indices | |
|---|---|---|---|---|---|---|---|
| % of DM | % of protein | mass (g) | % dry matter | % protein | % sludge | % cih | % cip |
| SP-311 | Alcalase ® 2.4 L | | | | | | |
| 0 | 0 | 91.88 | 8.11 | 2.99 | 16.8 | 80.9 | 66.3 |
| 1.6 | 0 | 92.8 | 7.94 | 3.10 | 16.8 | 83.8 | 71.3 |
| 1.6 | 0 | 86.3 | 7.95 | 3.10 | 21.0 | 85.0 | 73.5 |
| 0 | 2 | 95.7 | 8.75 | 3.45 | 13.8 | 87.3 | 76.6 |
| 1.6 | 2 | 104.1 | 9.23 | 3.78 | 11.2 | 98.7 | 89.6 |
| SP-348 | Alcalase ® 2.4 L | | | | | | |
| 1.6 | 0 | 114.4 | 6.37 | 3.00 | 20.3 | 65.3 | 68.0 |
| 1.6 | 2 | 123.0 | 7.33 | 3.38 | 14.6 | 75.1 | 76.4 |

The sludge content mentioned under indices is the actual content of sediment measured in the reaction mixture.

The indices calculated are centrifugation indices calculated as follows:

For dry matter:

$$cih = \frac{HC}{H} \times 100\%$$

where
  HC=% dry matter in centrifugate and
  H=% dry matter in the reaction mixture For protein:

$$cip = \frac{Pc}{P} \times 100\%$$

where
  PC=% protein in centrifugate
  P=% protein in reaction mixture.

As appears from the indices the solubilisation was increased to the highest values when both SP-311 and Alcalase® were used. SP-348 did not show as high solubilisation of neither dry matter nor protein as SP-311. Also the percentage of sludge content was the lowest when both SP-311 and Alcalase® were used.

EXAMPLE 3

Pilot plant trial: PP-958

1500 liters of potato fruit water was jet cooked at 130° C. by means of the Hydroheater® jet cooker (300 liters/hour including a holding cell of 25 liters). Thereby the holding time will be 5 minutes. The jet cooked product was immediately cooled to 50° C. and held for 30 minutes. Hereafter pH was elevated to pH=8.0 with 14.4 liters of 5.10N NaOH.

The hydrolysis by means of Alcalase® 2.4 L was carried out with a dosage of 0.5% of dry matter (E/D=0.5%). The hydrolysis was carried out to DH=10%, controlled by the pH-stat. During the reaction the viscosity, % sludge and °BRIX was measured.

Parallel with the above hydrolysis hydrolyses in the laboratory were also carried out. These reactions, which will be described in detail later in this example were followed without pH-stat, but by measuring of osmolality instead.

The next morning the pilot plant hydrolysate was evaporated on the Niro FF-200 falling film evaporator. During concentration samples were taken for measuring of viscosity using a Hake MV DIN measuring system.

Data from Pilot Plant

Enzyme 1: None, Dosage, % E/D: 0.00
Enzyme 2: Alcalase® 2.4 L, Dosage, % E/D: 0.50 Dosage, % E/P:1.05

Jet-cooking temperature: 130° C. with a holding time of 5 minutes.

Enzyme reaction:

TABLE 1

| DH-measurements | |
| --- | --- |
| % Nx6.25 | 1.85 |
| % dry matter | 3.86 |
| Reaction time (hours) | DH % (pH-stat) |
| 0.00 | 0.00 |
| 0.25 | 0.41 |
| 0.50 | 0.61 |
| 1.00 | 1.22 |
| 19.00 | 2.64 |

Viscosity measurements during evaporation

TABLE 2

| Dry matter and viscosity data from evaporation | | | | | |
| --- | --- | --- | --- | --- | --- |
| CONCENTRATE | | | Viscosity | Viscosity measurement | |
| liters | °Brix | °Brix (calc.) | mPa*s | Speed 1 | Speed 4 |
| 1250 | 3.8 | 3.8 | 1.25 | 1.50 | 0.00 |
| 780 |  | 6.1 | 1.25 | 1.50 | 0.00 |
| 550 |  | 8.6 | 1.25 | 1.50 | 0.00 |
| 360 |  | 13.2 | 1.67 | 2.00 | 0.00 |
| 250 | 30.1 | 19.0 | 4.18 | 3.00 | 0.50 |
| 200 | 32.6 | 23.8 | 5.85 | 4.00 | 0.75 |
| 150 | 33.7 | 31.7 | 7.52 | 5.00 | 1.00 |
| 100 | 45.1 | 47.5 | 27.56 | 17.00 | 4.00 |
| 50 | 55.6 | 95.0 | 303.11 | 155.00 | 52.00 |

Data from laboratory
Jet-cooking: 130° C. with a holding time of 5 minutes.
Trial I:
Enzyme 1: None, Dosage, % E/D: 0.00
Enzyme 2: Alcalase® 2.4 L, Dosage, % E/D: 0.50 Dosage, % E/P: 1.05
Enzyme 1: No reaction.
Enzyme 2: pH-stat, pH=8.50, 4.0N NaOH, T=50° C.
Enzyme reaction data:

TABLE 3

| DH-measurement | |
| --- | --- |
| % Nx6.25 | 1.85 |
| % dry matter | 3.86 |
| Reaction time (minutes) | DH % (pH-stat) |
| 390 | 6.08 |

Trial II:
Enzyme 1: Viscozyme® 120 L (product sheet B 456a-GB from Novo Nordisk A/S), Dosage, % E/D: 0.50
Enzyme 2: Alcalase® 2.4 L. Dosage, % E/D: 0.50 Dosage, % E/P: 1.05.
Enzyme 1: pH=4.81, T=50° C., Reaction time 1 hour
Enzyme 2: pH-stat, pH=8.50, 4.0N NaOH, T=50° C.

TABLE 4

| DH-measurement | |
| --- | --- |
| % Nx6.25 | 1.85 |
| % dry matter | 3.86 |
| Reaction time (hours) | DH % (pH-stat) |
| 2.40 | 7.18 |

A comparison between Table 3 and 4 shows that the combined use of a protease and a cell wall degrading enzyme generated a higher DH than the sole use of a protease.

EXAMPLE 4

This example was carried out in pilot plant.

1500 liters of potato fruit water was jet cooked at 130° C. by means of the Hydroheater® jet cooker (300 liters/hour including a holding cell of 25 liters). The holding time is 5 minutes. The jet cooked product was immediately cooled to 50° C. and held for 30 minutes. pH was measured and adjusted to pH=4.5 if above pH=5. 375 g of Viscozyme® 120 L (equivalent to 0.5% of dry matter) was added. The reaction was carried out for 1 hour. Hereafter pH was elevated to pH 8.0 by means of 18.6 liters of 5.10N NaOH. Hydrolysis by Alcalase® 2.4 L was carried out by means of a dosage of 0.5% of dry matter (E/D=0.5%). Also in this case 375 g of Viscozyme® 120 L was added. The hydrolysis was carried out to DH=10%, controlled by the pH-stat. During the reaction the viscosity, % sludge and °Brix was measured. The next morning the hydrolysate was evaporated on the Niro FF-200 falling film evaporator. During concentration samples were taken in order to measure the viscosity by means of a Hake MV DIN measuring system.

Enzyme 1: Viscozyme® 120 L, Dosage, % E/D: 0.50

Enzyme 2: Alcalase® 2.4 L, Dosage, % E/D: 0.50 Dosage, % E/P: 1.05

Reaction parameters:

Enzyme 1: pH=4.95, T=50° C., Reaction time: 1 hour

Enzyme 2: pH-stat, pH=8.00, 5.1N NaOH, T=50° C.

TABLE 5

DH-measurements

| % Protein | 1.85 | 1.85 |
| % dry matter | 3.86 | 3.86 |
| Reaction time (hours) | DH % (pH-stat) | DH % (osmometer) |
| --- | --- | --- |
| 1.00 | 0.14 | 0.00 |
| 2.00 | 0.49 | 0.00 |
| 2.50 | 0.81 | 7.44 |
| 2.67 | 0.94 | 7.44 |
| 18.50 | 4.07 | 20.30 |

Viscosity Measurements During Evaporation

TABLE 6

Dry matter and viscosity data from evaporation

| CONCENTRATE | | | Viscosity | Viscosity measurement | |
| --- | --- | --- | --- | --- | --- |
| liters | °Brix | °Brix (calc.) | mPa*s | Speed 1 | Speed 4 |
| 1200 | 8.0 | 8.0 | 9 | 11 | 0 |
| 1000 | 9.5 | 9.6 | 6 | 7 | 0 |
| 950 | 10.0 | 10.1 | 8 | 10 | 0 |
| 800 | 12.1 | 12.0 | 9 | 11 | 0 |
| 600 | 16.5 | 16.0 | 8 | 10 | 0 |
| 500 | 19.2 | 19.2 | 10 | 12 | 0 |
| 400 | 20.8 | 24.0 | 10 | 12 | 0 |
| 300 | 30.8 | 32.0 | 16 | 15 | 1 |
| 200 | 41.0 | 48.0 | 16 | 15 | 1 |
| 150 | — | 64.0 | 23 | 20 | 2 |
| 100 | 54.1 | 96.0 | 33 | 28 | 3 |
| 80 | 62.1 | 120.0 | 144 | 65 | 27 |
| 60 | 61.1 | 160.0 | 144 | 64 | 27 |

Due to the treatment with Viscozyme® 120 L a lower viscosity was found in the concentrated hydrolysate. Thereby it was possible to concentrate to a higher dry matter content before fouling appears on the evaporator tubes.

EXAMPLE 5

This example was carried out in pilot plant in order to illustrate the effect of various alkaline proteases.

The below indicated plan and flow-sheet was followed:

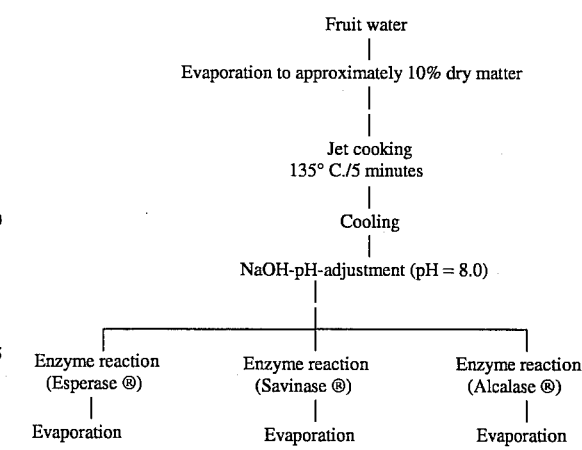

Procedure

To 785 liters of fruit water of 6.0° Brix was added 350 ml of antifoaming agent PP-2000. The mixture was vacuum evaporated on a falling film evaporator (Niro Atomizer type FF 200). The temperature of the product before calandria was 35°–40° C. and the temperature of the product leaving the calandria was 60°–65° C. After 190 minutes 427 liters of condensate and 358 liters of concentrate of 11.6° Brix was collected.

The concentrate was jet cooked in a Hydroheater® at T=135° C. with a holding time of 5 minutes. After a holding section the product was cooled to 50° C. through a plate heat exchanger to 50° C. By means of this method 324 kg of preconcentrated and jet cooked material was produced. The concentrate was analysed for dry matter (9.7% dry matter). Three portions each consisting of 108 kg of this heat treated concentrate was adjusted to pH=8.5 by means of 5N NaOH. Subsequently the heat treated and pH adjusted concentrate was enzyme treated with 0.5% of the alkaline proteases Esperase® 8.0 L type A, Savinase® 8.0 L or Alcalase® 2.4 L, respectively. During each hydrolysis samples were drawn as a function of the time, and 10 ml of the reaction mixture was centrifuged at 4200 rpm at a laboratory centrifuge. The supernatant was analysed for pH, osmolality, °Brix and % sludge.

After 240 minutes of reaction each of the hydrolysed mixtures were evaporated on a LUWA evaporator at a product temperature of 45°–60° C., until the viscosity of the concentrate increased to a value, at which the power consumption for the rotor of the LUWA evaporator was 3–4 times the value of the power consumption at the beginning of the evaporation.

The data for the three trial are shown in the following three tables:

| Time, minutes | pH | °Brix | Osmolality increase | % Sludge |
| --- | --- | --- | --- | --- |
| Enzyme: Esperase ® 8.0 L type A. | | | | |
| 1 | 8.48 | 9.7 | 2 | 17 |
| 10 | 8.45 | 9.7 | 8 | 16 |
| 30 | 8.41 | 9.8 | 17 | 16 |
| 60 | 8.39 | 10.1 | 17 | 15 |
| 90 | 8.36 | 10.1 | 25 | 14 |
| 120 | 8.30 | 10.3 | 24 | 14 |
| 150 | | 10.4 | 25 | 14 |
| 180 | | 10.9 | 35 | 13 |

-continued

| Time, minutes | pH | °Brix | Osmolality increase | % Sludge |
|---|---|---|---|---|
| 210 | | 10.6 | 34 | 14 |
| 240 | 8.22 | 10.7 | 33 | 14 |

Concentrate: 21 kg of 53.2° Brix.

Enzyme: Savinase ® 8.0 L

| Time, minutes | pH | °Brix | Osmolality increase | % Sludge |
|---|---|---|---|---|
| 0 | 8.50 | 9.6 | 0 | 18 |
| 1 | 8.48 | 9.7 | 6 | 18 |
| 10 | 8.46 | 9.7 | 1 | 17 |
| 30 | 8.38 | 9.9 | 9 | 17 |
| 60 | 8.32 | 9.9 | 18 | 17 |
| 90 | | 10.0 | 16 | 17 |
| 120 | | 10.2 | 21 | 15 |
| 150 | | 10.3 | 22 | 15 |
| 180 | | 10.3 | 17 | 15 |
| 210 | | 10.4 | 23 | 15 |
| 240 | 8.05 | 10.5 | 19 | 15 |

Concentrate: 13 kg of 56.9° Brix.

Enzyme: Alcalase ® 2.4 L

| Time, minutes | pH | °Brix | Osmolality increase | % Sludge |
|---|---|---|---|---|
| 1 | 8.52 | 9.6 | 0 | 18 |
| 10 | 8.46 | 9.8 | −4 | 18 |
| 30 | 8.41 | 9.9 | −7 | 17 |
| 60 | 8.32 | 10.3 | 9 | 17 |
| 90 | 8.24 | 10.5 | 10 | 17 |
| 120 | 8.20 | 10.6 | 6 | 17 |
| 150 | 8.14 | 10.9 | 38 | 16 |
| 180 | 8.10 | 11.0 | 31 | 16 |
| 210 | 8.05 | 11.2 | 38 | 14 |
| 240 | 8.02 | 11.3 | 68 | 14 |

Concentrate: 14 kg of 65.0° Brix.

Even in consideration of the fact that there were some uncertainty in the determination of the osmolality in the trial with Alcalase ®2.4 L it can be concluded that this trial showed a more effective degradation of the components of the potato fruit water in comparison to the two other alkaline proteases.

Documentation For Economic Superiority

In the following a typical embodiment of the method according to the invention is described, with emphasis upon the economic aspects thereof. Also, as comparison, a typical corresponding prior art method is described, also with emphasis upon the economic aspects thereof.

The embodiment of the method according to the invention is carried out as shown in the below indicated flow sheet.

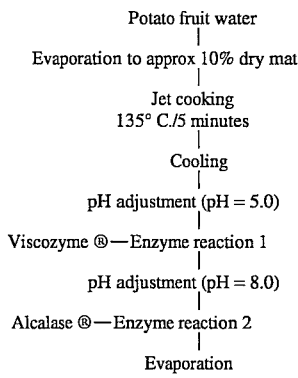

In more detail, this embodiment of the method according to the invention is carried out as follows.

1. Potato fruit water is evaporated to around 10° Brix by means of an evaporation temperature of 45°–60° C. The evaporation is carried out as a batch process with recirculation through the evaporator. During the evaporation the capacity (amount of condensate/minute), the temperature and the concentration in °Brix in the retentate is followed as a function of time.
2. The concentrate is jet cooked at 135° C. for 5 minutes. Samples for determination of osmolality, °Brix, pH and amount of sludge before and after jet cooking are taken. The total amount of dry matter is determined on a fast drier.
3. The reaction mixture is thermostatted at 50° C. The pH value is adjusted to 4.5–5.0. If above 5.0 the adjustment is made by means of phosphoric acid.
4. Viscozyme® is now added in a dosage of 0.50% Viscozyme®, based on dry matter. The reaction is followed with centrifuge samples in order to determine °Brix, osmolality and sludge volume. When the parameter values have levelled off (after around 2 hours), the reaction is stopped by adjustment of pH to 8.0 with NaOH.
5. Now hydrolysis is carried out without pH-stat by means of 0.5% Alcalase® 2.4 L, based on dry matter. This reaction, too, is followed by means of centrifuge samples for determination of °Brix, osmolality and sludge volume. When the parameter values have levelled off, the method is continued as indicated below, without inactivation.
6. The material is evaporated to approx. 50° Brix. During the evaporation samples are taken out from the concentrate tube, as a function of time, in order to determine the osmolality, °Brix, pH and sludge volume.

If the above indicated embodiment of the method according to the invention is based upon a throughput of 50 tons of potatoes/hour corresponding to 5,000 tons of potatoes/year, potato fruit water corresponding to approx. 56 m³/hour or 117,000 m³/year with a dry matter content of 3.5% will be produced.

If this amount of potato fruit water should be fed to the sewer (prior art method), treatment thereof in a biological purification plant would cost approx. 16–18 Danish kr./m³ or approx. 2,106,000 Danish kr./year.

The economic aspects in regard to the corresponding above indicated embodiment of the method according to the invention appear from the below list of items.

| | Danish kr. |
|---|---|
| Chemicals | |
| Antifoaming agents, 25 tons | 75,000 |
| NaOH pearls, 170 tons | 850,000 |
| Enzymes | |
| Viscozyme ®, 12.5 tons | 1,500,000 |
| Alcalase ®, 12.5 tons | 1,250,000 |
| Energy for evaporation | 1,100,000 |
| Salaries | 750,000 |
| Interest and provision for depreciation of an investment of 6 mio. Danish kr. | 1,200,000 |
| Total expenses | 6,725,000 |
| Expected income from sales of evaporated concentrate (8,200 tons with a price of 1.5 Danish kr./kg) | 12,300,000 |
| Profit, calculated in relation to prior art method | 7,681,000 |

It thus appears that the method according to the invention exhibits an economic superiority in comparison to prior art.

I claim:

1. Method for treatment of potato fruit water, wherein the potato fruit water is subjected to a heat treatment to at least 125° C. for at least 3 minutes, whereafter the heat treated potato fruit water is cooled to a temperature, at which enzymes are relatively stable, then enzymatically treated with a proteinase, and finally concentrated to microbial stability.

2. Method according to claim 1, wherein the potato fruit water is preconcentrated, either directly upstream the heat treatment or directly downstream the heat treatment.

3. Method according to claim 1, wherein the heat treatment is carried out in a jet cooker.

4. Method according to claim 1, wherein the potato fruit water is subjected to a heat treatment to at least 130° C. for at least 3 minutes, preferably for at least 5 minutes.

5. Method according to claim 1, wherein the heat treated potato fruit water is cooled to a temperature between 60° C. and 45° C.

6. Method according to claim 1, wherein the enzymatic treatment of the potato fruit water also comprises treatment with a starch degrading enzyme.

7. Method according to claim 1, wherein the enzymatic treatment of the potato fruit water also comprises treatment with a cell wall degrading enzyme.

8. Method according to claim 1, wherein the protease is a neutral or alkaline protease and wherein the enzymatic treatment is carried out at a constant pH at or close to the activity optimum of the enzyme.

9. Method according to claim 7, wherein the cell wall degrading enzyme is an SPS-ase preparation and the protease is Alcalase® protease.

10. Method according to claim 6, wherein the enzymatic treatment is carried out sequentially and with pH adjustment in order to obtain optimal activities of the enzymes.

11. Method according to claim 1, wherein the enzymatic reaction time is between 1 and 6 hours, preferably between 2 and 3 hours.

12. Method according to claim 1, wherein the enzyme or enzymes are not totally inactivated at the end of the enzymatic treatment.

13. Method according to claim 1, wherein the concentrated material is spraydried.

* * * * *